US00RE38314E

(19) United States
(12) Reissued Patent
Ager et al.

(10) Patent Number: US RE38,314 E
(45) Date of Reissued Patent: Nov. 11, 2003

(54) PROCESS FOR THE PREPARATION OF THE HERBICIDE ETHYL α-2-DICHLORO-5-[4-(DIFLUOROMETHYL)-4,5-DIHYDRO-3-METHYL-5-OXO-1H-1,2,4-TRIAZOL-1-YL]-4-FLUOROBENZENEPROPANOATE

(75) Inventors: John W. Ager, Princeton, NJ (US); Craig A. Polsz, Newtown, PA (US)

(73) Assignee: FMC Corporation, Philadelphia, PA (US)

(21) Appl. No.: 09/292,484

(22) Filed: Apr. 15, 1999

Related U.S. Patent Documents

Reissue of:
(64) Patent No.: 5,621,112
Issued: Apr. 15, 1997
Appl. No.: 08/683,444
Filed: Jul. 18, 1996

(51) Int. Cl.[7] ..... C07D 249/12
(52) U.S. Cl. ..... 548/263.2
(58) Field of Search ..... 548/263.2

(56) References Cited

U.S. PATENT DOCUMENTS 5,125,958 A 6/1992 Poss ..... 71/92

*Primary Examiner*—Patricia L. Morris
(74) *Attorney, Agent, or Firm*—FMC Corporation

(57) ABSTRACT

A process is disclosed for the preparation of the herbicide ethyl α-2-dichloro-5-[4-(difluoromethyl)-4,5-dihydro-3-methyl-5-oxo-1H-1,2,4-triazol-1-yl]-4-fluoro- benzenepropionate by the simultaneous diazotization of 4-difluoromethyl-4,5-dihydro-3-methyl-5-oxo-1-(5-amino-2-fluoro-4-chloro-phenyl)-1H-1,2,4-triazole (the Amine) and arylation of ethyl acrylate with the diazotized Amine. In the process the following reagents are added in sequence and, under specified conditions, to a cooled, stirred solution of the Amine in acetone: cuprous chloride, hydrochloric acid, ethyl acrylate, and sodium nitrite.

18 Claims, No Drawings

PROCESS FOR THE PREPARATION OF THE HERBICIDE ETHYL α-2-DICHLORO-5-[4-(DIFLUOROMETHYL)-4,5-DIHYDRO-3-METHYL-5-OXO-1H-1,2,4-TRIAZOL-1-YL]-4-FLUOROBENZENEPROPANOATE

Matter enclosed in heavy brackets [ ] appears in the original patent but forms no part of this reissue specification; matter printed in italics indicates the additions made by reissue.

This invention relates to an improved process for carrying out the last step in the preparation of the herbicide ethyl α-2-dichloro-5-[4-(difluoro-methyl)-4,5-dihydro-3-methyl-5-oxo-1H-1,2,4-triazol-1-yl]-4-fluorobenzenepropanoate, a Meerwein diazotization and arylation reaction.

The herbicide, which has the following structure,

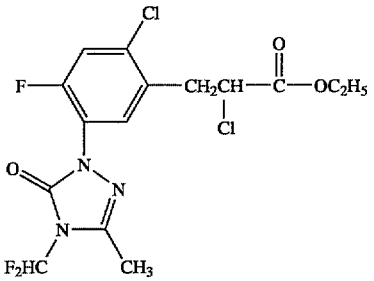

is disclosed and claimed in U.S. Pat. No. 5,125,958.

In common practice a Meerwein diazotization and arylation reaction is carried out in two steps. First, an arylamine is diazotized in an aqueous solution of e.g., sodium nitrite, and then the solution of diazotized amine is added to a solution of the compound to be arylated. In U.S. Pat. No. 5,125,958 the last step in the preparation of the herbicide involved diazotization of the amine 4-difluoromethyl-4,5-dihydro-3-methyl-5-oxo-1-(5-amino-2-fluoro-4-chlorophenyl)-1H-1,2,4-triazole. However, since it had been found that when one attempted to diazotize this amine in aqueous solution, the 2-fluoro substituent was lost by hydrolysis to the corresponding phenol. Accordingly, the diazotization described in the patent was carried out in the conventional two steps, but in nonaqueous medium, with t-butyl nitrite as the source of the nitrite. The diazotized amine was then added to ethyl acrylate (the arylation) to yield the desired herbicide. While this procedure is satisfactory for laboratory production on a small scale, it is not satisfactory for large scale, commercial production. Not only is the supply of t-butyl nitrite too limited, but large scale production would require handling large quantities of the diazo compound, an undesirably hazardous operation.

Surprisingly, it has now been found that under the proper conditions the diazotization and arylation can be carried out simultaneously, with aqueous sodium nitrite, without loss of the 2-fluoro substituent and in surprisingly good yields.

The diazotization/arylation reaction sequence is as follows:

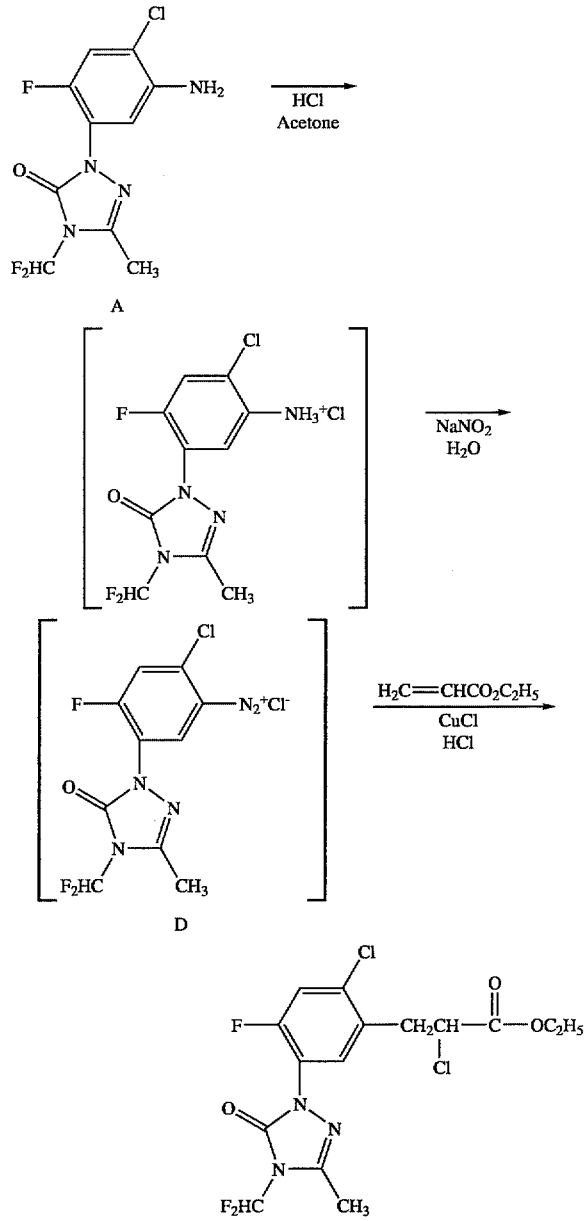

As noted above, in common practice the diazonium salt is first prepared and then added to the compound to be arylated. In the process of the invention the hydrochloride salt of the amine A is diazotized with sodium nitrite in the presence of ethyl acrylate, the material to be arylated. The diazonium chloride (D) produced by the diazotization of the amine hydrochloride with sodium nitrite reacts with ethyl acrylate in the presence of a catalytic amount of copper(I) chloride. The reaction is carried out at low temperature in acetone. The use of acetone as the solvent allows the use of sodium nitrite in a minimum of water. Acetone also facilitates the recycling of the copper(I) chloride catalyst. Another advantage of the process is that the fact that the diazotization acrylation reactions are occurring simultaneously minimizes the probability of the diazotization product reacting with itself.

The process starts with the preparation of a solution of the amine A in acetone, preferably in an inert atmosphere, e.g. nitrogen. A useful ratio of acetone to amine is in the range of 10 to 30 equivalents of acetone to one equivalent of amine, preferably 20 to 25 equivalents of acetone to one of amine. The solution may be filtered to remove any insoluble material that may be present. To the amine solution is added, with stirring, a Meerwein arylation catalyst, for example, copper(I) chloride or copper(II) chloride, preferably copper (I) chloride, and, again, an inert atmosphere is preferred. (Stirring is maintained throughout the course of the reaction.) The amount of copper(I) chloride is important in the process of the present invention. If too little is used, the reaction is slower, and the yield of the final product is lower. Too much copper(I) chloride in the reaction mixture results in dechlorination of the final product. Therefore, a useful ratio of copper(I) chloride to amine is in the range of 0.05 to 1.0 equivalent of copper(I) chloride to one equivalent of amine, preferably 0.1 to 0.15 equivalent to one. The reaction mixture is then cooled to below 0° C., preferably to about −10° C., and the amine salt is prepared by addition of concentrated hydrochloric acid, or anhydrous hydrogen chloride, preferably anhydrous hydrogen chloride added below the surface of the reaction mixture. During the addition the reaction mixture is maintained at a temperature of −20° C. to 30° C., preferably −10° C. to 10° C. The preparation of the amine salt requires about 30 to 120 minutes, preferably about 45 to 90 minutes. The amount of ethyl acrylate that is next added to the amine salt slurry is important. A large excess of ethyl acrylate is required to obtain optimum yields from this process. If the excess is reduced, the yield of final product is reduced. A useful ratio of ethyl acrylate to amine has been found to be 5 to 20 equivalents of ethyl acrylate to one equivalent of amine, preferably 10 to 15 equivalents to one. The time needed to add the ethyl acrylate is relatively unimportant. However, the reaction mixture temperature is maintained below 10° C. throughout the addition and is controlled to some degree by the addition of the ethyl acrylate. The reaction mixture is then brought to about 0° C., and an aqueous solution of sodium nitrite is added to the reaction mixture. This step is a critical step in the process of the present invention. The diazotization/arylation reactions are occurring simultaneously. During the diazotization step water must be kept to a minimum. A large amount of water results in hydrolysis of the diazo intermediate, yielding a phenol by-product. To minimize the production of by-products a useful ratio of sodium nitrite to amine is in the range of 1.0 to 2.0 equivalents of sodium nitrite to one equivalent of amine, preferably 1.4 to 1.7 equivalents to one. To keep the amount of water to a minimum, it is advantageous to use a concentrated aqueous solution of sodium nitrite for the diazotization step. A saturated aqueous solution of sodium nitrite contains about 40% (wt/wt) of sodium nitrite. A useful concentration of the aqueous solution of sodium nitrite is, therefore, about 20% to 40% (wt/wt) sodium nitrite, preferably 35% to 40% sodium nitrite. Reaction mixture temperatures are also important in optimizing the diazotization/arylation reaction. Temperatures above 10° C. increase the probability of by-product formation. A useful range of reaction mixture temperatures for the optimization of the process step is −10° C. to 20° C., preferably 0° C. to 10° C. The rate of addition of the aqueous sodium nitrite solution is also important in optimizing yield. Fast rates of addition in the process of the present invention result in lower yields of product. The optimum rate of addition requires about 1 to 6 hours, preferably 2 to 3 hours. The addition of the aqueous sodium nitrite solution is done below the surface of the stirred reaction mixture. The reaction mixture is then stirred for a period of 15 to 90 minutes, preferably 20 to 40 minutes, to allow completion of the reaction. At this point crude yields of product in the range of 80–88% are obtained. The purity of the product may be improved by washing, followed by distillation. During the washing step the temperature is maintained at about −10° C. to 20° C., preferably 5° C. to 10° C., and in the preferred washing sequence the reaction mixture is washed first with a dilute aqueous acid, for example, 5% hydrochloric acid, then with a dilute aqueous base, for example 5% sodium hydroxide, and finally with a sodium chloride solution. Upon completion of the wash steps, the volatile material in the reaction mixture, i. e., acetone/ethyl acrylate, may be removed at a pot temperature of 30° C. to 80° C., preferably 40° C. to 65° C., under a reduced pressure of 20 mm to 70 mm Hg, preferably 45 mm to 55 mm Hg. The removal of volatile material is considered complete when the ethyl acrylate concentration is below about five percent. Ethyl acrylate is known to polymerize under certain conditions. As a precautionary measure, an antioxidant and a free-radical inhibitor are added to the distillation overhead system. There is, however, no evidence that polymerization occurs in the reaction vessel during the reaction, wash steps, or during removal of the volatile material.

For further purification of the product the non-volatile material containing the reaction product may be distilled in a shod path evaporaror or wiped-film still. In order to increase the efficiency of the distillation process, the reaction product may be passed (degassing step) through the still at an evaporator temperature of 100° C. to 140° C. and a pressure of 10 mm to 20 mm Hg, preferably 120° C. to 130° C. and a pressure of 13 mm to 18 mm Hg, to remove any remaining ethyl acrylate or other low-boiling materials. The degassed reaction product may then be passed once through the still at an evaporator temperature of 160° C. to 180° C. and a pressure of 1.0 mm to 5.0 mm Hg, preferably 170° C. to 180° C. and a pressure of 1.0 mm to 2.0 mm Hg. The non-volatile material from the first pass through the still may then be passed a second time through the still at an evaporator temperature of 160° C. to 200° C. and a pressure of 0.03 mm to 1.0 mm Hg, preferably 160° C. to 180° C. and a pressure of 0.03 mm to 0.5 mm Hg. The rate of feed through the still will be governed by the size of the still. It is understood that the conditions for degassing and distillation will vary, depending on the apparatus used. Operation under preferred conditions has given a typical percent yield of distilled ethyl α-2-dichloro-5-[4-(difluoromethyl)-4,5-dihydro-3-methyl-5-oxo-1H-1,2,4-triazol-1-yl]-4-fluorobenzenepropanoate of 75–80% (based on the amount of starting amine); at a purity of about 91% (as determined by high pressure liquid chromatography).

EXAMPLE 1

Preparation of Ethyl α-2-Dichloro-5-[4-(Difluoromethyl)-4,5-Dihydro-3-Methyl-5-Oxo-1H-1,2,4-Triazol-1-Yl]-4-Fluoro-Benzenepropanoate, Laboratory Scale A two-liter, jacketed resin flask was fitted with a thermometer, nitrogen inlet tube, outlet tube connected to a carbon trap (to minimize the escape of the odor of ethyl acrylate), and a fitting consisting of an eight-inch, large bore, teflon-coated hypodermic needle attached to a 50 mL syringe that was in turn connected to a syringe pump. In a separate vessel, 140.4 grams (0.46 mole-1.0 equiv.) of 4-difluoromethyl-4,5-dihydro-3-methyl-5-oxo-1-(5-amino-2-fluoro-4-chlorophenyl)-1H-1,2,4-triazole was dissolved in 600 grams (10.33 moles-22.5 equiv.) of acetone. The solution was cooled to 0° C., and filtered into the resin flask. With stirring, 56.2 grams (1.54 moles-3.4 equiv.) of anhydrous hydrogen chloride gas was then bubbled into the triazole/acetone solution during a 15–20 minute period. Upon completion of the addition 6.1 grams (0.06 mole-0.13 equiv.) of copper(I) chloride was added. With continued stirring the reaction mixture was cooled to 0° C. under a nitrogen atmosphere, and 640.4 grams (6.33 moles-13.8 equiv.) of ethyl acrylate was added. The reaction mixture was again cooled to 0° C., and a solution of 48.1 grams (0.69 mole-1.5 equiv.) of sodium nitrite dissolved in 88.1 grams (4.9 moles-10.7 equiv.) of water was added. The nitrite/water solution was added to the reaction mixture at a rate of about 0.48 mL/minute from the syringe, with the needle outlet below the surface of the reaction mixture. The complete addition required about 3.75 hours, after which time the reaction mixture was stirred for an additional 45 minutes at 0° C. The reaction was then quenched with 200 mL of water, after which the reaction mixture was stirred for about 15 minutes. The organic layer was separated and washed with one portion of each of 200 mL of aqueous 1N hydrochloric acid, 200 mL of water. and a 1:1 mixture of aqueous 5% sodium hydroxide and ethyl acetate wherein the volume of sodium hydroxide solution and ethyl acetate were each equal to the volume of the organic layer. The organic layer was then concentrated at 70° C. under vacuum, yielding 193.3 grams (assay—84.6%, crude yield—86.4%) of ethyl a-2-dichloro-5-[4-(difluoromethyl)-4,5-dihydro-3-methyl-5-oxo-1H-1.2,4-triazol-1-yl]-4-fluorobenzenepropanoate. The concentrated product was passed through a two-inch, 0.25 $ft^2$ Pope Wiped-Film Still at 160° C. at 0.8 mm Hg to remove lower boiling impurities. The non-volatile material was passed a second time through the wiped-film still at 220° C./1 mm Hg to distill the product from high-boiling impurities, yielding 134.9 grams (assay-92%, distilled yield-65.6%) of ethyl α-2-dichloro-5-[4-(difluoromethyl)-4,5-dihydro-3-methyl-5-oxo-1H-1,2,4-triazol-1-yl]-4-fluorobenzenepropanoate.

EXAMPLE 2

Preparation of Ethyl α-2-Dichloro-5-[4-(Difluoromethyl)-4,5-Dihydro-3-Methyl-5-Oxo-1H-1,2,4-Triazol-1-YL]-4-Fluorobenzenepropanoate, Pilot Plant Scale Several batches of product were prepared according to the following procedure. Acetone, 457.4 pounds (7.89 lb-moles, 22 equiv.) was charged by pressure differential into a 200 gallon jacketed reactor, followed by 107 pounds (0.36 lb-mole, 1.0 equiv.) of 98% 4-difluoromethyl-4,5-dihydro-3-methyl-5-oxo-1-(5-amino-2-fluoro-4-chlorophenyl)-1H-1,2,4-triazole. The mixture was stirred and optionally filtered at ambient temperature to remove solid impurities. The solution was recharged into the 200 gallon reactor, stirred, and purged with nitrogen. To this was then added 4.6 pounds (0.05 lb-mole, 0.13 equiv.) of copper(I) chloride. Upon completion of the addition the mixture was cooled to about −10° C. by circulating a cold brine solution through the jacket of the reactor. The reactor was closed, and the nitrogen purge was stopped. Anhydrous hydrogen chloride, 32.7 pounds (0.9 lb-mole, 2.5 equiv.), was then bubbled in below the surfane of the reaction mixture at a rate of about 0.55 lb/min., while the temperature of the reaction mixture was maintained between −10° C. and 10° C. The complete addition required about one hour. Upon completion of addition, the reactor was opened to atmospheric pressure. The reaction mixture temperature was then brought to about 0° C., and 484 pounds (4.84 lb-moles, 13.5 equiv.) of ethyl acrylate was added by gravity. Upon completion of the addition a solution of 37.1 pounds (4.84 lb-moles, 1.5 equiv.) of sodium nitrite in 69 pounds (3.83 lb-moles, 10.6 equiv.) of water was added at a rate of about 0.6 pound/minute, below the surface of the reaction mixture. The reaction mixture temperature was maintained between 0° C. and 5° C. The complete addition required about three hours, after which time the reaction mixture was stirred for 30 minutes. While the reaction mixture temperature was kept between 5° C. and 10° C., the reaction mixture was washed in turn with 147 pounds of water, 146.8 pounds of aqueous 5% hydrochloric acid, 153 pounds of aqueous 5% sodium hydroxide, and 150 pounds of water. The ethyl acrylate and acetone were then removed from the reaction mixture by distillation at about 65° C./50 mm Hg. To prevent polymerization the distilled ethyl acrylate and acetone mixture was stabilized by a solution consisting of 0.18 pound of 4-methoxyphenol, 0.18 pound of phenothiazine, and 56 pounds of toluene, which was circulated through the condenser and distillate receiver. The temperature of the residue-product was maintained at about 45° C. as it was drummed for future use. The yield of crude product, ethyl-α-2-dichloro-5-[4-(difluoromethyl)-4,5-dihydro-3-methyl-5-oxo-1H-1,2,4-triazol-1-yl]-4-fluorobenzenepropanoate, was 152.2 pounds. A number of batches prepared as described above were combined. The combination was passed through a wiped-film distillation still, first under low vacuum to remove low-boiling material (degassed), then twice under high vacuum to obtain distilled product. The following conditions were used with the wiped-film still:

| | Degassing Step | First Pass | Second Pass |
|---|---|---|---|
| Feed Temp (° C.) | 60 | 65 | 65 |
| Evaporator Temperature (° C.) | 125 | 175 | 193 |
| Condenser Coolant (° C.) | −2 | 70 | 60 |
| Agitator speed (rpm) | 425 | 425 | 425 |
| Vacuum (mm Hg) | 15 | 0.6 | 0.5 |

The percent yield of distilled ethyl α-2-dichloro-5-[4-(difluoromethyl)-4,5-dihydro-3-methyl-5-oxo-1H-1,2,4-Triazol-1-yl]-4-fluorobenzenepropanoate was 65% (based on the amount of starting amine); purity was 91% (as determined by means of high pressure liquid chromatography).

EXAMPLE 3

Preparation of Ethyl α-2-Dichloro-5-[4-(difluoromethyl)-4,5-Dihydro-3-Methyl-5-Oxo-1H-1,2,4-triazol-1-Yl]-4-Fluoro-Benzenepropanoate, Pilot Plant Scale Several batches of product were prepared according to the following procedure. A 1000 gallon jacketed reactor was purged with nitrogen, and 510.0 pounds (1.71 lb-moles, 1.0 equiv.) of 98% 4-difluoromethyl-4,5-dihydro-3-methyl-5-oxo-1-(5-amino-2-fluoro-4-chlorophenyl)-1H-1,2,4-triazole was charged into the reactor. To this was then charged 22.0 pounds (0.22 lb-mole, 0.13 equiv.) of copper(I) chloride. The reactor was sealed and again purged with nitrogen. Acetone, 2178.8 pounds (37.57 lb-moles, 22.0 equiv.) was then charged into the reactor by means of a positive displacement pump. Upon completion of the addition the mixture was stirred and cooled to between −10° C. and 0° C. by circulating a cold brine solution through the jacket of the reactor. Anhydrous hydrogen chloride, 155.8 pounds (4.27 lb-mole, 2.5 equiv.), was then bubbled in below the surface of the reaction mixture at a rate of about 2.5 lb/min., while the reaction mixture temperature was held below 10° C. The anhydrous hydrogen chloride addition time was typically completed in one to two hours. Upon completion of the hydrogen chloride feed the reactor was vented to atmospheric pressure. The reaction mixture temperature was then brought to about 0° C., and 2305.2 pounds (23.1 lb-moles, 13.5 equiv.) of ethyl acrylate was charged into the reactor by means of a positive displacement pump. Upon completion of the addition 441.8 pounds of an aqueous 40 weight percent (2.56 lb-mole, 1.5 equiv.) sodium nitrite solution was charged below the surface of the reaction mixture at a rate of about 1.8 lbs/minute. The reaction mixture temperature was maintained between 0° C. and 5° C. The complete addition required about four hours, after which time the reaction mixture was stirred for 30 minutes. The reaction was considered complete when the amount of unreacted amine (solvent free) remaining in the reaction mixture was less than about 0.5 area percent by gas chromatography. Upon completion of the reaction the reaction mixture was maintained at 5° C. to 10° C. and washed with two portions of 700 pounds each of an aqueous 5% hydrochloric acid solution, two portions of 729 pounds each of an aqueous 5% sodium hydroxide solution, and one portion of 715 pounds of an aqueous 10% sodium chloride solution. The ethyl acrylate and acetone were then removed from the reaction mixture by distillation at between 65° C. and 75° C. at less than 10 mm Hg, until the concentration of ethyl acrylate in the solution was less than about five percent. To prevent polymerization, the ethyl acrylate and acetone mixture distillate was stabilized by a solution consisting of 0.21 pound of 4-methoxyphenol, 0.21 pound of phenothiazine, and 28 pounds of toluene, which was circulated through the condenser and distillate receiver. The temperature of the residue-product was maintained at about 45° C. as it was drummed for future use. The yield of crude product, ethyl α-2-dichloro-5-[4-(difluoromethyl)-4,5-dihydro-3-methyl-5-oxo-1H-1,2,4-triazol-1-yl]-4-benzenepropanoate, from this reaction at this point was typically about 82%. A number of batches prepared as described above were combined. The, combination was passed through a short path evaporator (SPE), first under low vacuum to remove low-boiling material (degassing), then twice under high vacuum to obtain distilled product. The following conditions were used with the SPE:

| | Degassing Step | First Pass | Second Pass |
|---|---|---|---|
| Feed Temp (° C.) | 65 | 65 | 65 |
| Evaporator Temperature (° C.) | 100 | 170 | 170 |
| Condenser Coolant (° C.) | −30 | 70 | 70 |
| Agitator speed* (rpm) | 200 | 200 | 200 |
| Vacuum (mm Hg) | 10 | 2.8 | 0.28 |

*The agitator speed will vary depending on the size of the SPE; these figures are for an 8 $ft^2$ SPE.

The percent yield of ethyl α-2-dichloro-5-[4-(difluoromethyl)-4,5-dihydro-3-methyl-5-oxo-1H-1,2,4-triazol-1-yl]-4-fluorobenzenepropanoate distilled was 80% (based on the amount of starting amine); purity was 91% (as determined by high pressure liquid chromatography).

We claim:

1. A process for the preparation of [ethyl α2-dichloro-5-[4-(difluoro-methyl)-4,5-dihydro-3-methyl-5-oxo-1H-1,2,4-triazol-1-yl]-4-fluorobenzenepropionate (the Product)] *formula (I)* by the simultaneous diazotization of 4-difluoromethyl-4,5-dihydro-3-methyl-5-oxo-1-(5-amino-2-fluoro-4-chlorophenyl)-1H-1,2,4-triazole (the Amine) and arylation of ethyl acrylate with the diazotized Amine, *wherein formula (I) is:*

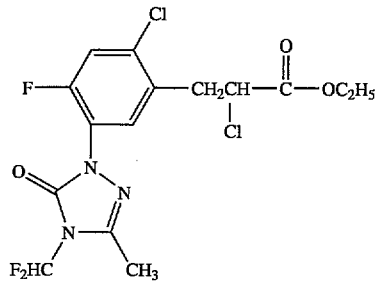

which [consists of] *process comprises* the following steps in which the amounts of all components other than the Amine are given in molar equivalents relative to one molar equivalent of the Amine:

(a) adding *a Meerwein arylation catalyst* to a stirred solution of the Amine in 10 to 30 equivalents of acetone [0.05 to 0.5 equivalents of cuprous chloride];

[(b) cooling the solution to a temperature in the range of −20° to 30° C. and maintaining the temperature in that range while stirring and adding sufficient hydrochloric acid to convert the Amine to the hydrochloride salt;]

*(b) maintaining the temperature in the range of −20° to 30° C. and adding a sufficient amount of hydrogen chloride to form a salt of the Amine;*

(c) maintaining the temperature below about 10° C[.] while adding [to the resultant slurry, with stirring,] 5 to 20 equivalents of ethyl acrylate;

(d) bringing the temperature of the stirred reaction mixture to about 0° C[.] and adding 1.0 to 2.0 equivalents of sodium nitrite over a period of 1 to 6 hours while maintaining the temperature below about 20° C[.] and then continuing stirring for 15 to 90 minutes; *and*

(e) recovering [the Product] *formula (I)*.

2. The process of claim 1 in which step (d) is followed by [a washing step in which the temperature is maintained in the range of 0° to 20° C., while the reaction mixture is washed successively with dilute aqueous acid, dilute aqueous base, and an aqueous solution of sodium chloride] *at least one washing step.*

3. The process of claim 2 in which steps (a) [and (b)]–*(d)* are carried out under an inert atmosphere; 20 to 25 equivalents of acetone are used in step (a); the temperature in step (b) is −10° to 10° C[.], and the hydrochloric acid is anhydrous; 10 to 15 equivalents of ethyl acrylate are added in step (c); in step (d) 1.4 to 1.7 equivalents of sodium nitrite are added as an aqueous solution containing 20 to 40 weight percent sodium nitrite [over a period of 2 to 3 hours] at a temperature below about 10° C[., and the post addition stirring is for 20 to 40 minutes]; and [in] the *temperature of the at least one* washing step [the temperature] is maintained [at 5° to 10° C., the aqueous acid is 5% hydrochloric acid, and the aqueous base is 5% sodium hydroxide] *in the range of 0° to 20° C.*

*4. The process of claim 1, wherein said Meerwein arylation catalyst is selected from the group consisting of cuprous chloride and cupric chloride.*

*5. The process of claim 4, wherein said Meerwein arylation catalyst is cuprous chloride.*

*6. A process for the preparation of formula (I):*

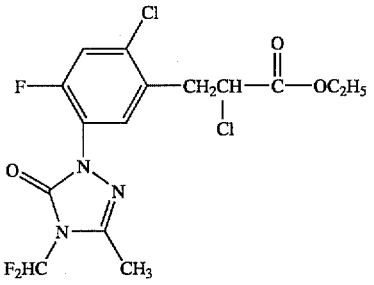

*comprising: (i) forming a diazotized salt of 4-difluoromethyl-4,5-dihydro-3-methyl-5-oxo-1-(5-amino-2-fluoro-4-chlorophenyl)-1H-1,2,4-triazole by reacting a salt of 4-difluoro-methyl-4,5-dihydro-3-methyl-5-oxo-1-(5-amino-2-fluoro-4-chlorophenyl)-1H-1,2,4-triazole with sodium nitrite; and (ii) simultaneously reacting said diazotized salt of 4-difluoro-methyl-4,5-dihydro-3-methyl-5-oxo-1-(5-amino-2-fluoro-4-chlorophenyl)-1H-1,2,4-triazole, as it is produced in step (i), with ethyl acrylate in the presence of a Meerwein arylation catalyst to obtain said formula (I).*

*7. The process of claim 6, wherein said Meerwein arylation catalyst is selected from the group consisting of cuprous chloride and cupric chloride, and said reactions (i) and (ii) proceed in an aqueous medium.*

*8. A process for the preparation of formula (I):*

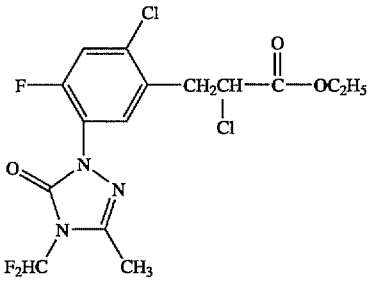

*comprising the step of adding aqueous sodium nitrite to a solution comprising a salt of 4-difluoro-methyl-4,5-dihydro-3-methyl-5-oxo-1-(5-amino-2-fluoro-4-chlorophenyl)-1H-1,2,4-triazole, ethyl acrylate, and a Meerwein arylation catalyst to form formula (I).*

*9. The process of claim 8, wherein said Meerwein arylation catalyst is selected from the group consisting of cuprous chloride and cupric chloride, and said solution is aqueous.*

*10. The process of claim 9, wherein said solution contains acetone.*

*11. The process of claim 8, wherein said ethyl acrylate is added in 5 to 20 equivalents to one equivalent of said salt of 4-difluoro-methyl-4,5-dihydro-3-methyl-5-oxo-1-(5-amino-2-fluoro-4-chlorophenyl)-1H-1,2,4-triazole.*

*12. The process of claim 8, wherein said aqueous sodium nitrite is added in 1.0 to 2.0 equivalents of said salt of 4-difluoro-methyl-4,5-dihydro-3-methyl-5-oxo-1-(5-amino-2-fluoro-4-chlorophenyl)-1H-1,2,4-triazole.*

*13. The process of claim 8, wherein said ethyl acrylate is added in 5 to 20 equivalents to one equivalent of said salt of 4-difluoro-methyl-4,5-dihydro-3-methyl-5-oxo-1-(5-amino-2-fluoro-4-chlorophenyl)-1H-1,2,4-triazole, and said aqueous sodium nitrite is added in 1.0 to 2.0 equivalents of said salt of 4-difluoro-methyl-4,5-dihydro-3-methyl-5-oxo-1-(5-amino-2-fluoro-4-chlorophenyl)-1H-1,2,4-triazole.*

*14. The process of claim 10, wherein said ethyl acrylate is added in 5 to 20 equivalents to one equivalent of said salt of 4-difluoro-methyl-4,5-dihydro-3-methyl-5-oxo-1-(5-amino-2-fluoro-4-chlorophenyl)-1H-1,2,4-triazole, and said aqueous sodium nitrite is added in 1.0 to 2.0 equivalents of said salt of 4-difluoro-methyl-4,5-dihydro-3-methyl-5-oxo-1-(5-amino-2-fluoro-4-chlorophenyl)-1H-1,2,4-triazole.*

*15. The process of claim 14, wherein said ethyl acrylate and aqueous sodium nitrite are added at a temperature below 10° C.*

*16. The process of claim 6, wherein the simultaneous reaction in step (ii) further occurs in the presence of hydrochloric acid or anhydrous hydrogen chloride.*

*17. The process of claim 8, wherein said solution further contains hydrochloric acid or anhydrous hydrogen chloride.*

*18. The process of claim 6, wherein said salt of 4-difluoro-methyl-4,5-dihydro-3-methyl-5-oxo-1-(5-amino-2-fluoro-4-chlorophenyl)-1H-1,2,4-triazole is a hydrochloride salt of 4-difluoro-methyl-4,5-dihydro-3-methyl-5-oxo-1-(5-amino-2-fluoro-4-chlorophenyl)-1H-1,2,4-triazole.*

* * * * *